United States Patent
Rakshit et al.

(10) Patent No.: US 11,061,254 B2
(45) Date of Patent: Jul. 13, 2021

(54) ADJUSTING CONTACT LENS PRESCRIPTION WHILE WEARING LENS

(71) Applicant: INTERNATIONAL BUSINESS MACHINES CORPORATION, Armonk, NY (US)

(72) Inventors: Sarbajit K. Rakshit, Kolkata (IN); James E. Bostick, Cedar Park, TX (US); Martin G. Keen, Cary, NC (US); John M. Ganci, Jr., Raleigh, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 61 days.

(21) Appl. No.: 16/256,545

(22) Filed: Jan. 24, 2019

(65) Prior Publication Data
US 2020/0241324 A1 Jul. 30, 2020

(51) Int. Cl.
| | |
|---|---|
| *G02C 7/00* | (2006.01) |
| *G02C 5/00* | (2006.01) |
| *G02C 13/00* | (2006.01) |
| *G02C 7/04* | (2006.01) |
| *G06F 3/01* | (2006.01) |
| *A61B 3/00* | (2006.01) |
| *A61B 3/113* | (2006.01) |

(Continued)

(52) U.S. Cl.
CPC ............ *G02C 7/047* (2013.01); *A61B 3/0025* (2013.01); *A61B 3/113* (2013.01); *G02C 7/027* (2013.01); *G06F 3/013* (2013.01); *G02B 2027/014* (2013.01)

(58) Field of Classification Search
CPC ... G02C 7/04; G02C 7/02; G02C 5/00; G02C 7/06; G02C 7/061; A61B 3/103; A61B 3/14; A61B 3/113; A61B 3/125; A61B 3/024; A61B 3/032; A61B 3/1015; A61B 3/107
USPC ...... 351/159.02, 41, 159.01, 159.03, 159.05, 351/159.06, 178, 200, 205–206, 209–210, 351/219, 222, 223, 246, 247
See application file for complete search history.

(56) References Cited

U.S. PATENT DOCUMENTS

| | | | |
|---|---|---|---|
| 6,078,380 A | * | 6/2000 | Taniguchi .............. G03B 27/68 355/52 |
| 6,851,805 B2 | | 2/2005 | Blum |

(Continued)

FOREIGN PATENT DOCUMENTS

CN 103543537 A 1/2014

OTHER PUBLICATIONS

M. Elgan, "Why a smart contact lens is the ultimate wearable," May 9, 2016 [Accessed Feb. 12, 2018] https://www.computerworld.com/article/3066870/wearables/why-a-smart-contact-lens-is-the-ultimate-wearable.html.

(Continued)

*Primary Examiner* — Dawayne Pinkney
(74) *Attorney, Agent, or Firm* — Brian M. Restauro, Esq.; Wayne F. Reinke, Esq.; Heslin Rothenberg Farley & Mesiti P.C.

(57) ABSTRACT

Changing a prescription of a contact lens includes analyzing vision-related data regarding a user (e.g., eye measurements and/or contextual information) to determine a currently needed contact lens prescription, resulting in a determined contact lens prescription; and adjusting a contact lens prescription of a contact lens embedded in the user's eye based on the determined contact lens prescription.

20 Claims, 8 Drawing Sheets

(51) Int. Cl.
*G02C 7/02* (2006.01)
*G02B 27/01* (2006.01)

(56) References Cited

U.S. PATENT DOCUMENTS

| | | | |
|---|---|---|---|
| 9,292,973 | B2 | 3/2016 | Bar-Zeev |
| 9,392,129 | B2 | 7/2016 | Simmons |
| 9,465,237 | B2 | 10/2016 | Tate |
| 9,500,884 | B2 | 11/2016 | Egan |
| 9,690,099 | B2 | 6/2017 | Bar-Zeev |
| 9,690,118 | B2 | 6/2017 | Etzkorn |
| 9,933,634 | B2 | 4/2018 | Wiser |
| 10,133,090 | B2 | 11/2018 | Jiang |
| 10,338,275 | B1 * | 7/2019 | Acosta ............... G02B 5/285 |
| 10,643,392 | B2 | 5/2020 | Schowengerdt |
| 2004/0027536 | A1 | 2/2004 | Blum |
| 2004/0156021 | A1 * | 8/2004 | Blum ............... A61B 3/0285 351/233 |
| 2012/0140167 | A1 | 6/2012 | Blum |
| 2012/0154277 | A1 | 6/2012 | Bar-Zeev |
| 2012/0268712 | A1 | 10/2012 | Egan et al. |
| 2014/0306866 | A1 | 10/2014 | Miller |
| 2015/0185503 | A1 * | 7/2015 | Tate ............... G02C 7/083 351/158 |
| 2015/0339570 | A1 | 11/2015 | Scheffler |
| 2015/0362756 | A1 | 12/2015 | Wiser |
| 2016/0026253 | A1 | 1/2016 | Bradski |
| 2016/0091737 | A1 | 3/2016 | Kim |
| 2016/0252748 | A1 | 9/2016 | Jiang |
| 2016/0299354 | A1 | 10/2016 | Shtukater |
| 2017/0023793 | A1 | 1/2017 | Shtukater |
| 2017/0192253 | A1 | 7/2017 | Rubinstein et al. |
| 2017/0227792 | A1 | 8/2017 | Starner |
| 2017/0270636 | A1 | 9/2017 | Shtukater |
| 2018/0045965 | A1 | 2/2018 | Schowengerdt |
| 2018/0110614 | A1 | 4/2018 | Hyde |
| 2018/0373058 | A1 | 12/2018 | Bostick |

OTHER PUBLICATIONS

Anonymous, "Emacula" [Accessed Feb. 12, 2018] http://www.emacula.io/.

L. Greenemeier, "Computerized Contact Lenses Could Enable In-Eye Augmented Reality," Nov. 23, 2011, [Accessed Feb. 12, 2018] https://blogs.scientificamerican.com/observations/computerized-contact-lenses-could-enable-in-eye-augmented-reality/.

J. Hong, et al., "See-through optical combiner for augmented reality head-mounted display: index-matched anisotropic crystal lens," Scientific Reports, Jun. 5, 2017, pp. 1-11.

H. Hua, et al., "A 3D integral imaging optical see-through headmounted display," Jun. 2, 2014, vol. 22, No. 11, DOI:10.1364/OE.22.013484, Optics Express, pp. 13484-13491.

Anonymous, "Variable focussing spectacles for patients with intraocular lenses," IP.com, Prior Art Database Technical Disclosure, Feb. 4, 2005, IPCOM000042880D, pp. 1-2.

N. Lee, "Avegant's light-field tech gives hope to a mixed-reality future," May 1, 2017 [Accessed Feb. 11, 2018] https://www.engadget.com/2017/05/01/avegant-light-field-hands-on/.

N. Padmanaban, et al. "Optimizing virtual reality for all users through gaze-contingent and adaptive focus displays," PNAS, Feb. 28, 2017, vol. 114, No. 9, pp. 2183-2188.

International Search Report and Written Opinion dated May 9, 2020 for International Application No. PCT/IB2020/050231 filed on Jan. 13, 2020.

List of IBM Patents or Patent Applications Treated as Related, Nov. 19, 2020, pp. 1-2.

* cited by examiner

ADJUSTING CONTACT LENS PRESCRIPTION WHILE WEARING LENS

BACKGROUND

The present disclosure generally relates to contact lenses and, more particularly, to multifocal contact lenses.

Multifocal contact lenses exist with certain capabilities. Currently available are Multifocal IOLs (Intraocular Lenses), which achieve near and distance vision by having two (bifocal) or three (trifocal) focal points simultaneously. The function of multifocal IOL depends on the pupil size for refractive types. The concept is based on the principle that the pupil tends to constrict for near tasks, so the central portion of the lens is designed for near and the outer portion for distance. For diffractive types of multifocal IOLs, light is split by diffraction and the vision is pupil independent.

Multifocal contact lens designs in today's art include simultaneous vision designs with primary viewing zones, and there are also designs for segmented multifocal designs where the bottom portion of the contact may be for near sight and the top and center for far sight (similar to bifocal glasses).

SUMMARY

Shortcomings of the prior art are overcome and additional advantages are provided through the provision, in one aspect, of a computer-implemented method. The method includes: analyzing vision-related data regarding a user to determine a currently needed contact lens prescription, resulting in a determined contact lens prescription; and adjusting a contact lens prescription of a contact lens embedded in the user's eye based on the determined contact lens prescription.

In another aspect, a contact lens may be provided. The contact lens includes: a spherical shell having at least one slot therein; a first magnification disk corresponding to a first prescription, the first magnification disk sized to fit within one or more of the at least one slot; and a mechanism to move the first magnification disk into and out of the one or more of the at least one slot.

In yet another aspect, a contact lens may be provided. The contact lens includes: one or more processors; one or more reservoirs containing liquid that is released, by the one or more processor, based on vision-related data regarding a user; and a switching mechanism for adjusting, by the one or more processor, a contact lens prescription of the contact lens based on the vision-related data regarding the user.

Further, services relating to one or more aspects are also described and may be claimed herein.

Additional features are realized through the techniques set forth herein. Other embodiments and aspects, including but not limited to methods, computer program product and system, are described in detail herein and are considered a part of the claimed invention.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Disclosed is a method to analyze: by measurement of eye lens shape and dimension(s); or contextually based on what a user is looking at, and adjust a contact lens prescription (also referred to as "Rx") based on the measurements (direction of the user's view, focal point of user's eye gaze and the distance of the focal point) or based on the contextual information, the adjusting being automatic, controlled by the user, based on mode setting, etc. Eye gaze technology and, for example, cameras as well as other techniques are used to accurately determine a focal distance of a user and determine whether a far-sighted prescription or a near-sighted prescription should be engaged. Provided are embodiments on how the switching of the lens works. For example, a communication mechanism may be used allowing the contact lenses to receive signals from the user through a remote, app or application that may, for example, tell the contact lens to remain in one mode (one prescription) or the other until further instructed.

Approximating language that may be used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value.

As used herein, the terms "may" and "may be" indicate a possibility of an occurrence within a set of circumstances; a possession of a specified property, characteristic or function;

and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

Spatially relative terms, such as "beneath," "below," "lower," "above," "upper," and the like, may be used herein for ease of description to describe one element's or feature's relationship to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" other elements or features would then be oriented "above" or "over" the other elements or features. Thus, the example term "below" may encompass both an orientation of above and below. The device may be otherwise oriented (e.g., rotated 90 degrees or at other orientations) and the spatially relative descriptors used herein should be interpreted accordingly. When the phrase "at least one of" is applied to a list, it is being applied to the entire list, and not to the individual members of the list.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable storage medium(s) having computer readable program code embodied thereon.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

A user may have multiple prescriptions including, for example, a prescription for near-sightedness and one for far-sightedness. Multifocal contact lenses include both prescriptions in each lens. The problems associated to the techniques of today with multifocal contacts include unclear images, blurry vision and image displacement. The present disclosure addresses the problems associated with current multifocal contact lenses by allowing for automatic adjustment between multiple prescriptions of a user while wearing the contact(s).

There are two major aspects to the process disclosed herein, starting with analysis (via measurement or contextual) for which prescription to implement, and then performing the actual switch to the necessary prescription. In one embodiment, the analysis aspect of the present disclosure takes the form of determining: a direction in which the user is looking; a focal point of eye gaze of the user; and a focal distance of an object in the eye gaze of the user.

Figure 1:
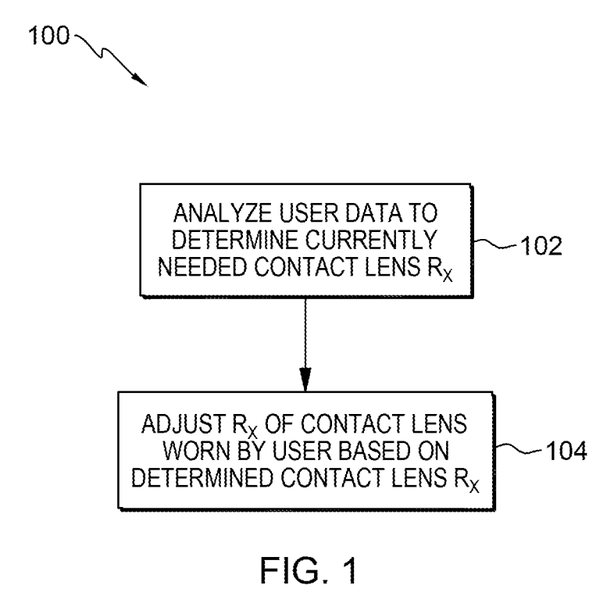
FIG. 1 is a flow diagram for one example of a computer-implemented method of adjusting a prescription of a smart contact lens, in accordance with one or more aspects of the present disclosure.

FIG. 1 is a flow diagram 100 for one example of a computer-implemented method of automatically adjusting a contact lens between at least two prescriptions of a user, in accordance with one or more aspects of the present disclosure. Initially, a data processing system in communication with the contact lens analyses to determine 102 a direction, a focal point of an eye gaze of the user and a focal distance of an object in the eye gaze of the user. Based on the determined direction, focal point and focal distance, the contact lens prescription is adjusted 104.

Aspects of the embodiments herein include, for example, the use of eye gaze technology, which may be included as an enabling technology in the present disclosure. Smart contact lenses exist with an integrated camera. The camera would be very small and, and in one embodiment, integrated on an inner surface of the contact lens near the edge of the contact lens so that it doesn't obscure the user's vision. By being part of the contact lens, the camera would naturally follow eye gaze, allowing for a range of applications. This technology may be used as a means of more accurately following a user's gaze to determine if the user is looking at something close or further away.

By being part of the contact lens, the camera would naturally follow your gaze, allowing for a huge range of applications, and this disclosure is one of those applications, using the enabling art. Direction is not just the direction of the face of the person, but also adjusted per the other component which figured out eye gaze.

Figure 2:
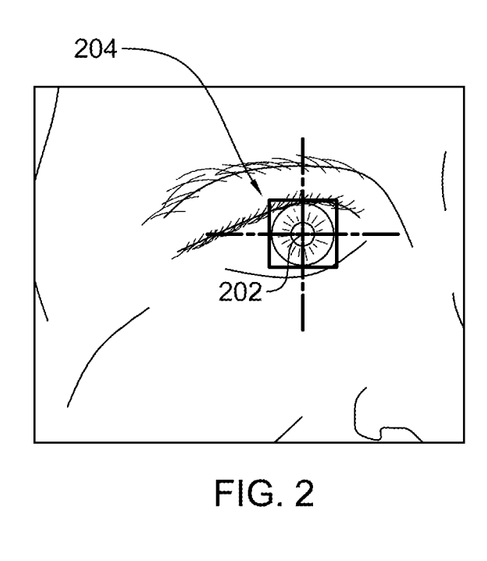
FIG. 2 depicts one example of eye gaze based on eye-direction percentage from center, in accordance with one or more aspects of the present disclosure.

FIG. 2 depicts one example of determining eye gaze based on, for example, eye-direction percentage from a center point 202 of an eye 204, in accordance with one or more aspects of the present disclosure. In one embodiment, the integrated camera(s) may include an adjustment capability, for example, to determine eye-gaze. If the eye is looking slightly up (pupils are in a high position) or the eyeballs are looking to the right as oriented to the face, or if they are looking down or to the left, then the eye-gaze determination may make use of this to adjust a position of the camera(s). For example, while the face is looking straight forward and the pupils are 10 percent to the right of a normal straight ahead gaze, then the camera(s) could be adjusted to the right in the same way. Likewise for up, down, left, or any combination.

Once the direction of eye gaze is determined, cameras or other technology can be used to determine focal distance (e.g., the distance of the first object in the noted direction). This is the object in the current view of the user. One example of determining a focal distance is to use the thin lens equation (e.g., Gaussion form); that is:

$$\frac{1}{O} + \frac{1}{I} + \frac{1}{F}$$

where O=object distance, I=image distance and F=focal length.

Figure 3:
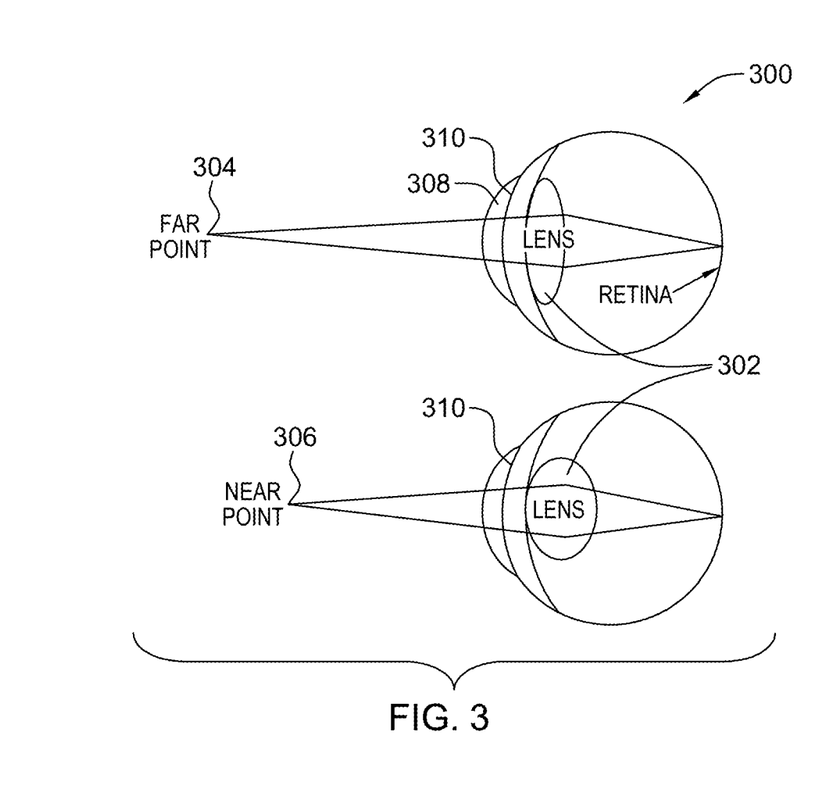
FIG. 3 depicts one example of obtaining a direction of sight using an inner camera measuring lens, in accordance with one or more aspects of the present disclosure.

Another embodiment can measure the inner eye lens for direction. See FIG. 3, which obtains a direction of sight using an inner camera measuring lens. FIG. 3 depicts changes 300 in the shape of an eye lens 302 at a relatively far point 304 and a relatively near point 306. As shown, the lens is naturally flatter when looking at the far point and more oval (less flat) when looking at the near point. In one embodiment, a smart contact lens 308 includes one or more camera 310 on an inner surface of the smart contact lens toward the outer edge of the contact, to avoid or minimize interfering with the user's sight.

Once the focal distance is known, the proper prescription can be ascertained by the distance of the object, where, in one example, a manufactured pre-set distance (i.e., threshold) or, in another example, may be configurable and, for example, possibly be overridden by the user. In one example, where a threshold is used, anything below the threshold of a certain distance gets one prescription, and everything else gets a second prescription.

In another embodiment, the analysis aspect takes the form of gathering vision-related contextual information regarding what the user is looking at and/or what the user is doing. For example, location, movement, acceleration, sound, and light (generally, sensor-based information), may be obtained from, for example, a smart phone or other device paired with a smart contact as described herein.

Analysis to determine what the user is looking at, in one embodiment, may include the use of outwardly facing miniaturized cameras or video recording devices. These micro cameras may be adjustable, for example, be turned to face a particular direction. This direction is not just the direction of the face of the person, but may also be adjusted per the eye gaze determination.

Embodiments herein further include, for example, wireless communications capabilities, to and from the contact lenses described herein via, for example, radio frequency technology (e.g., RFID) or other technology. For example, short-range communication protocols could be used including, e.g., Bluetooth and Near-Field Communication (NFC). Such communications may be used, in addition to system use, for the user-control embodiment where the user sets a mode for the contact lens.

In one embodiment, the lenses are configurable via a computing device, mobile device, app or other electronic device to turn on the automation or to temporarily set the mode to keep a particular prescription, for example, a near-sighted or far-sighted prescription. The contacts could be set up as such before going in the user's eye, or during use, via wireless communications described subsequently in more detail to update the system.

Once the proper prescription has been determined, the contacts will need to switch to the necessary prescription. However, in one embodiment, the system may first confirm a switch in prescriptions is necessary, for example, because the user is looking at something further or closer, thus crossing the threshold into the other (or another) prescription.

The following details embodiments of how a switch of prescriptions may take place.

In one embodiment, existing technology can be used to fill liquid in the lenses as necessary. In one example employing existing technology, flexible lenses may employ an electromechanical mechanism (e.g., using piezoelectric technology) to cause a desired curvature. A pair of flexible membranes encasing a refractive liquid may be used in conjunction with the electro-mechanical mechanism to achieve a desired contact lens prescription. As another example of the use of liquid in contact lenses, scleral contacts are large-diameter gas permeable contact lenses specially designed to vault over the entire corneal surface and rest on the "white" of the eye (sclera). In doing so, scleral lenses functionally replace the irregular cornea with a perfectly smooth optical surface to correct vision problems caused by keratoconus and other corneal irregularities. Also, the space between the cornea and the back surface of a scleral lens acts as a fluid reservoir to provide comfort for people with severe dry eyes who otherwise could not tolerate contact lens wear. Scleral contacts are noticeably larger than standard gas permeable (GP) contacts and have a diameter equal to or greater than that of soft contact lenses. More complex conditions, including advanced keratoconus, pathologically dry eyes or severe ocular surface disease that might require a large tear reservoir, often are fitted with larger scleral lenses, as they have more capacity to hold fluid or bridge large changes in corneal curvature.

In another embodiment, layers may be set up where the contact is made up of an outside body as normal, but incorporates one or more slot where glass or other material can be slid in from a top, side or other section of the contact area (normally a bit out of the range of the pupil or sight) and electronically slid into "center stage" where that particular prescription glass will be in front of the pupil and thus in use. For example, a contact lens may be shaped as normal, and inside the shell of the contact lens there may be one or two empty slots for various prescriptions to be inserted. The insert spot is, for example, at the top end of the of the contact and not covering the full size and shape of the entire contact, but only large enough to be useful in the "wheelhouse" of the sight vision direction, that is to say, directly in front of the pupil and slightly larger than the pupil in its largest possible size. There would be tracks in each slot whereby the prescription glass or appropriate other transparent material in that position would be able to quickly slide down into position or up and out of the way. Systematic signals could be sent by the system so that the contact knows which prescription slides in, and which one slides out.

Figure 9:
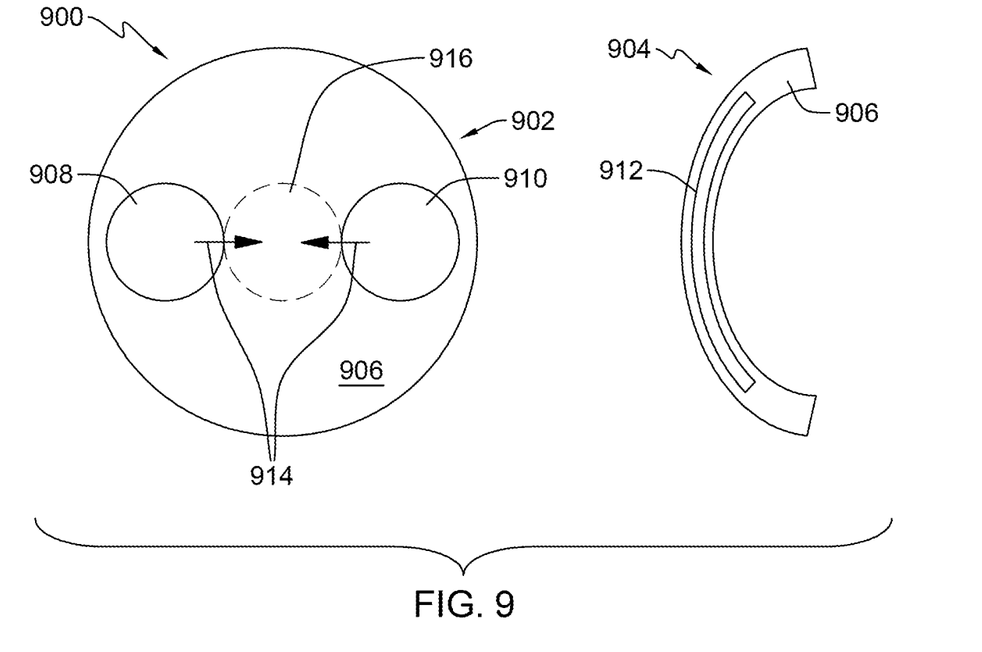
FIG. 9 depicts one embodiment of a contact lens including a front view and a side view, in accordance with one or more aspects of the present disclosure.

FIG. 9 depicts one example of a contact lens 900 including a front view 902 and a side view 904, in accordance with one or more aspects of the present disclosure. The contact lens includes, for example, an outer shell 906 and two magnification disks 908 and 910, each of which sits within a slot 912 and can be slid 914 via a sliding mechanism (not shown) into a center 916 of the lens covering, for example, the pupil (obscured by contact lens) when worn by a user. In one embodiment, the sliding mechanism may include a piezoelectric actuator for both small size and low power needs. In one example, each magnification disk corresponds to a different contact lens prescription. Only one of the magnification disks may, in one example, be slid into the center at a time. In another embodiment, one or both magnification disks may slide into the center, together producing a third prescription combined. In another embodiment, there may be one or two magnification disks and the lens body itself in the center may correspond to a prescription on its own.

Figure 10:
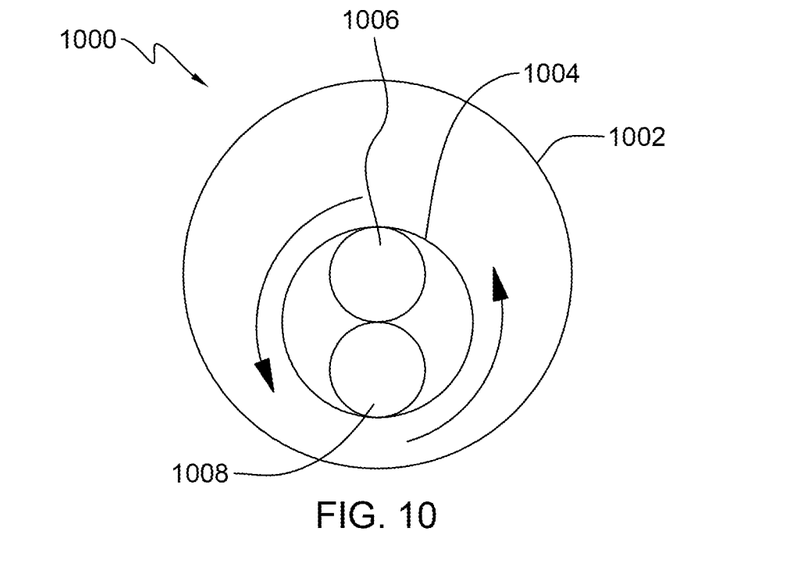
FIG. 10 depicts another embodiment of a contact lens, in accordance with one or more aspects of the present disclosure.

FIG. 10 depicts another embodiment of a contact lens 1000, in accordance with one or more aspects of the present disclosure. The contact lens includes, for example, a lens body 1002 and a magnification "wheel" 1004 housed therein. The magnification wheel includes, for example, two magnification disks 1006 and 1008, each of which corresponds to a contact lens prescription. The magnification wheel rotates 1010 via a rotation mechanism (obscured) based on the analysis aspect above to place one of the magnification disks at a center of the lens body in front of the pupil.

Figure 4:
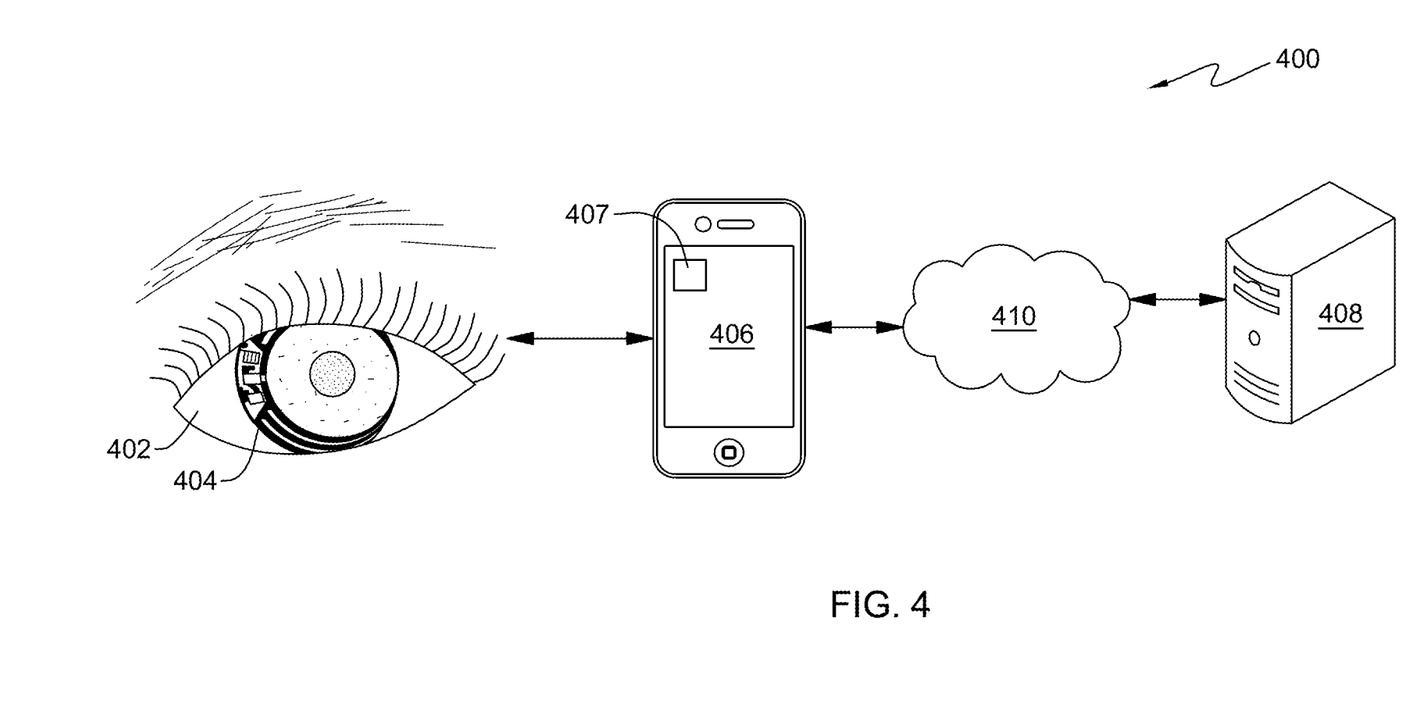
FIG. 4 is block diagram of one example of a communications network to enable communications between a contact embedded in a user's eye and a system driving switching between contact lens prescriptions, in accordance with one or more aspects of the present disclosure.

FIG. 4 is block diagram of one example of a communications network 400 to enable communications between a contact 404 as disclosed herein, embedded in a user's eye 402, and a system. In this example, the contact is paired to a smart phone 406 (e.g., via Bluetooth to an application 407) in order to communicate with system 408 (e.g., a server) over, for example, the Internet 410 or other global communications network. In another embodiment, the contact may be in communication with a smart phone not connected to the system over the internet. In still another embodiment, the contact is autonomous, for example, the components are small enough that outside processing is not necessary.

Figure 5:
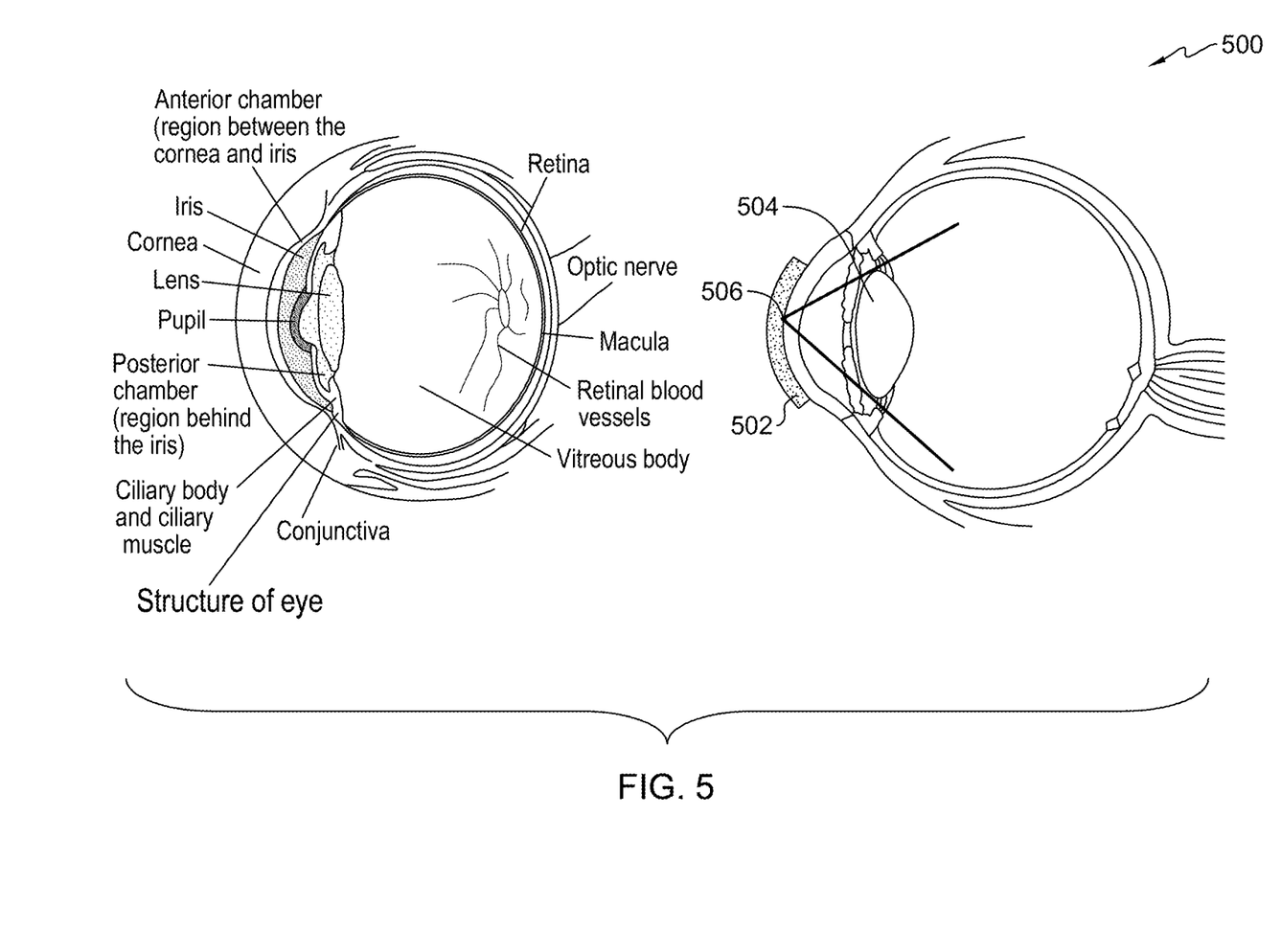
FIG. 5 depicts one example of a human eye wearing a contact lens, in accordance with one or more aspects of the present disclosure.

FIG. 5 depicts one example of a human eye 500 wearing a contact lens 502 as disclosed herein. The lens 504 of the eye is measured for shape and dimensions by camera 506 (e.g., digital, informed, etc.) placed, for example, at or near an inner edge of the contact outside the user's vision. In one embodiment, the focal distance and focal point can be calculated from other data. For example, one way of determining a focal distance is to use the thin lens equation (e.g., Gaussion form); that is:

$$\frac{1}{O} + \frac{1}{I} + \frac{1}{F}$$

where O=object custance (i.e., distance of object to the center of eye lens), I=image distance (i.e., the distance from lens center to where an image is formed) and F=focal length (i.e., the distance of the lens at rest to the retina).

Based on the methods described above, the prescription is automatically or selectably changed. Example embodiments have been provided, but the invention is not limited to those. A new technique for changing a contact lens prescription in situ, for example, changing the shape of a contact lens or some other method may come along that could be used to accomplish changing the prescription. The present disclosure seeks to capture all such techniques.

In a first aspect, disclosed above is a computer-implemented method. The computer-implemented method includes: analyzing vision-related data regarding a user to determine a currently needed contact lens prescription, resulting in a determined contact lens prescription; and adjusting a contact lens prescription of a contact lens embedded in the user's eye based on the determined contact lens prescription.

In one example, the vision-related data may include, for example, a direction, a focal point of an eye gaze of the user, and a focal distance of an object in the eye gaze of the user. In one example, the adjusting may be, for example, automatic based on a threshold for the focal distance.

In one example, the analyzing may include, for example, measuring an eye lens of the user.

In one example, the adjusting may be, for example, one of automatic and controllable by the user.

In one example, the analyzing may include, for example, using camera(s) disposed on the contact lens.

In one example, the adjusting may be, for example, one of filling the contact lens embedded in the user's eye with liquid solution, triggering a sliding mechanism to move spherical shaped material(s) that matches the user's prescription based on the determined direction, focal point and focal distance of an object in the user's gaze, and rotating a center portion of the contact lens.

In one example, the vision-related data in the computer-implemented method of the first aspect may include, for example, vision-related contextual information regarding a current activity of the user, and the analyzing may include, for example, cognitively analyzing the vision-related contextual information. In one example, the adjusting may be, for example, one of automatic and controllable by the user.

In one example, the analyzing may include, for example, using camera(s) disposed on the contact lens.

In one example, the adjusting may be, for example, one of filling the contact lens embedded in the user's eye with liquid solution, triggering a sliding mechanism to move one or more spherical shaped material that matches the user's prescription based on the determined direction, focal point and focal distance of an object in the user's gaze, and rotating a center portion of the contact lens.

In a second aspect, disclosed above is a contact lens. The contact lens includes a spherical shell having slot(s) therein; a first magnification disk corresponding to a first prescription, the first magnification disk sized to fit within one or more of the slot(s); and a mechanism to move the first magnification disk into and out of the one or more of the slot(s).

In one example, the slot(s) may include, for example, at least two slots, the contact lens may further include, for example, a second magnification disk corresponding to a second prescription different than the first prescription, the second magnification disk sized fit within a second slot of the at least two slots, and wherein the mechanism also moves the second magnification disk into and out of the second slot.

In one example, the spherical shell of the contact lens of the second aspect may have, for example, second magnification corresponding to a second prescription different from the first prescription.

In one example, the spherical shell of the contact lens of the second aspect may have, for example, a second magnification and a combination of the second magnification and the first magnification may correspond to a second prescription different from the first prescription.

In a third aspect, disclosed above is a contact lens. The contact lens includes processor(s); reservoir(s) containing liquid that is released, by the processor(s), based on vision-related data regarding a user; and a switching mechanism for adjusting, by the processor(s), a contact lens prescription of the contact lens based on the vision-related data regarding the user.

In one example, the contact lens may include, for example, a center portion that is fillable, the center portion shaped by an amount of the liquid released.

In one example, the adjusting of the contact lens of the third aspect may be, for example, one of automatic and controllable by the user.

In one example, the vision-related data of the contact lens of the third aspect may be, for example, one of: a determined direction, a focal point of a user's gaze and a focal distance of an object in the user's gaze; and vision-related contextual information regarding a current activity of the user.

In one example, the contact lens of the third aspect may further include, for example, camera(s) disposed on the contact lens for providing the vision-related data.

Certain embodiments herein may offer various technical computing advantages involving computing advantages to address problems arising in the realm of computer networks. Various decision data structures can be used to drive artificial intelligence (AI) decision making, such as decision data structure that cognitively performs one or more function described herein. Decision data structures as set forth herein can be updated by machine learning so that accuracy and reliability is iteratively improved over time without resource consuming rules intensive processing. Machine learning processes can be performed for increased accuracy and for reduction of reliance on rules based criteria and thus reduced computational overhead. For enhancement of computational accuracies, embodiments can feature computational platforms existing only in the realm of computer networks such as artificial intelligence platforms, and machine learning platforms. Embodiments herein can employ data structuring processes, e.g. processing for transforming unstructured data into a form optimized for computerized processing. Embodiments herein can examine data from diverse data sources. Embodiments herein can include artificial intelligence processing platforms featuring improved processes to transform unstructured data into structured form permitting computer based analytics and decision making. Embodiments herein can include particular arrangements for both collecting rich data into a data repository and additional particular arrangements for updating such data and for use of that data to drive artificial intelligence decision making.

In one example, a cognitive computer system performs a cognitive function as described herein. In general, the term "cognitive computing" (CC) has been used to refer to new hardware and/or software that mimics the functioning of the human brain and helps to improve human decision-making, which can be further improved using machine learning. In this sense, CC is a new type of computing with the goal of more accurate models of how the human brain/mind senses, reasons, and responds to stimulus. CC applications link data analysis and adaptive page displays (AUI) to adjust content for a particular type of audience. As such, CC hardware and applications strive to be more effective and more influential by design.

Some common features that cognitive systems may express include, for example: ADAPTIVE—they may learn as information changes, and as goals and requirements evolve. They may resolve ambiguity and tolerate unpredictability. They may be engineered to feed on dynamic data in real time, or near real time; INTERACTIVE—they may interact easily with users so that those users can define their needs comfortably. They may also interact with other processors, devices, and Cloud services, as well as with people; ITERATIVE AND STATEFUL—they may aid in defining a problem by asking questions or finding additional source input if a problem statement is ambiguous or incomplete. They may "remember" previous interactions in a process and return information that is suitable for the specific application at that point in time; and CONTEXTUAL—they may understand, identify, and extract contextual elements such as meaning, syntax, time, location, appropriate domain, regulations, user's profile, process, task and goal. They may draw on multiple sources of information, including both structured and unstructured digital information, as well as sensory inputs (e.g., visual, gestural, auditory and/or sensor-provided).

Various decision data structures can be used to drive artificial intelligence (AI) decision making. Decision data structures as set forth herein can be updated by machine learning so that accuracy and reliability is iteratively improved over time without resource consuming rules intensive processing. Machine learning processes can be performed for increased accuracy and for reduction of reliance on rules based criteria and thus reduced computational overhead.

For enhancement of computational accuracies, embodiments can feature computational platforms existing only in the realm of computer networks such as artificial intelligence platforms, and machine learning platforms. Embodiments herein can employ data structuring processes, e.g. processing for transforming unstructured data into a form optimized for computerized processing. Embodiments herein can examine data from diverse data sources such as data sources that process radio or other signals for location determination of users. Embodiments herein can include artificial intelligence processing platforms featuring improved processes to transform unstructured data into structured form permitting computer based analytics and decision making. Embodiments herein can include particular arrangements for both collecting rich data into a data repository and additional particular arrangements for updating such data and for use of that data to drive artificial intelligence decision making.

As used herein, terms used taking the form of "cognitive <function>" refers to the use of cognitive computing in performing the function for users in real-time. Cognitive computing is the simulation of human thinking, using software and/or hardware, which may be enhanced/improved using machine learning. Machine learning is based in mathematics and statistical techniques, giving computer systems the ability to "learn" with data provided, e.g., a relatively large amount of data, without the need to be explicitly programmed. The goal of cognitive computing is to create automated systems capable of solving problems without human assistance, broadly referred to as Artificial Intelligence (AI).

Artificial intelligence (AI) refers to intelligence exhibited by machines. Artificial intelligence (AI) research includes search and mathematical optimization, neural networks and probability. Artificial intelligence (AI) solutions involve features derived from research in a variety of different science and technology disciplines ranging from computer science, mathematics, psychology, linguistics, statistics, and neuroscience.

Where used herein, the term "real-time" refers to a period of time necessary for data processing and presentation to a user to take place, and which is fast enough that a user does not perceive any significant delay. Thus, "real-time" is from the perspective of the user.

Figure 6:
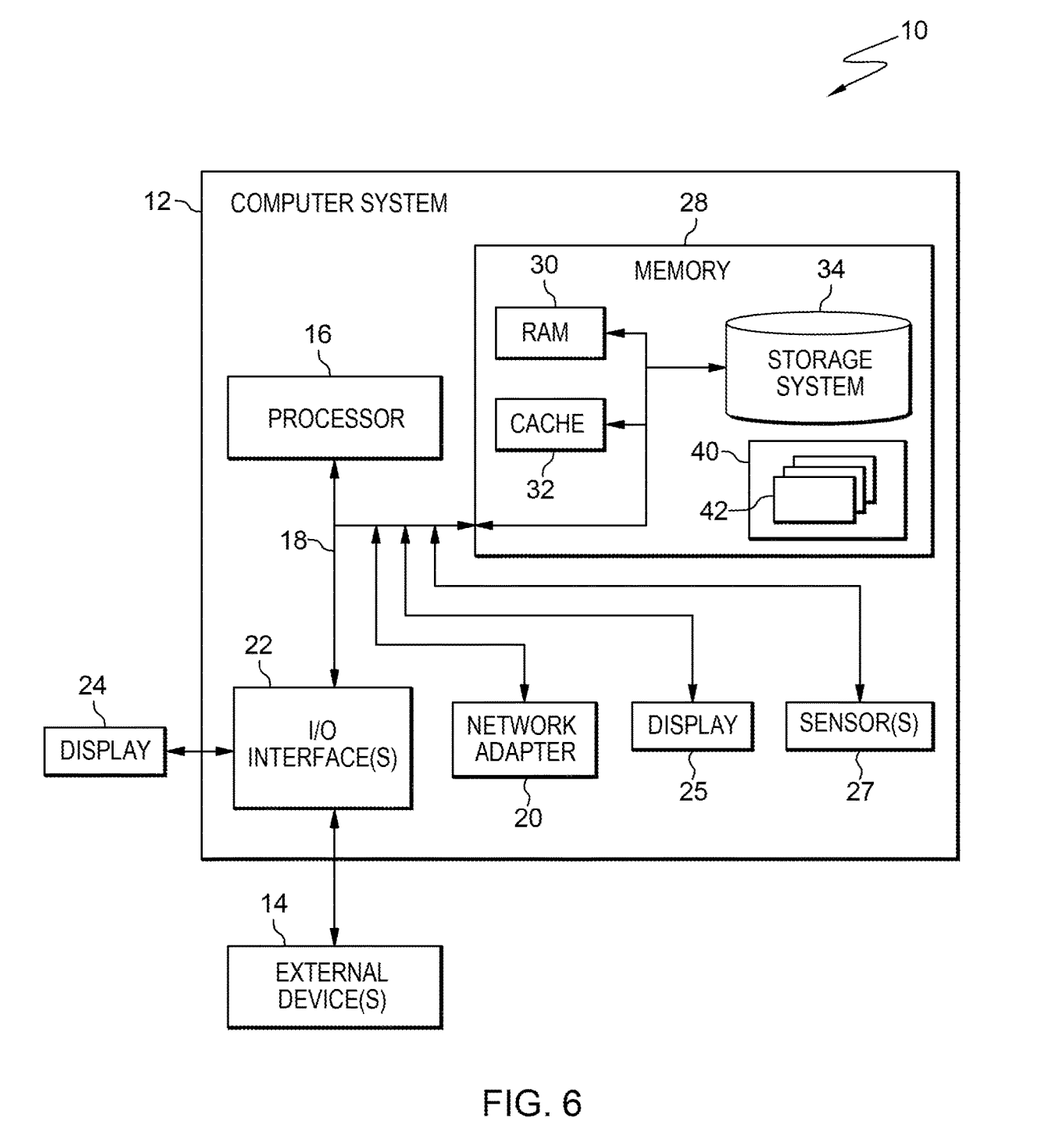
FIG. 6 is a block diagram of one example of a computer system, in accordance with one or more aspects of the present disclosure.
Figure 7:
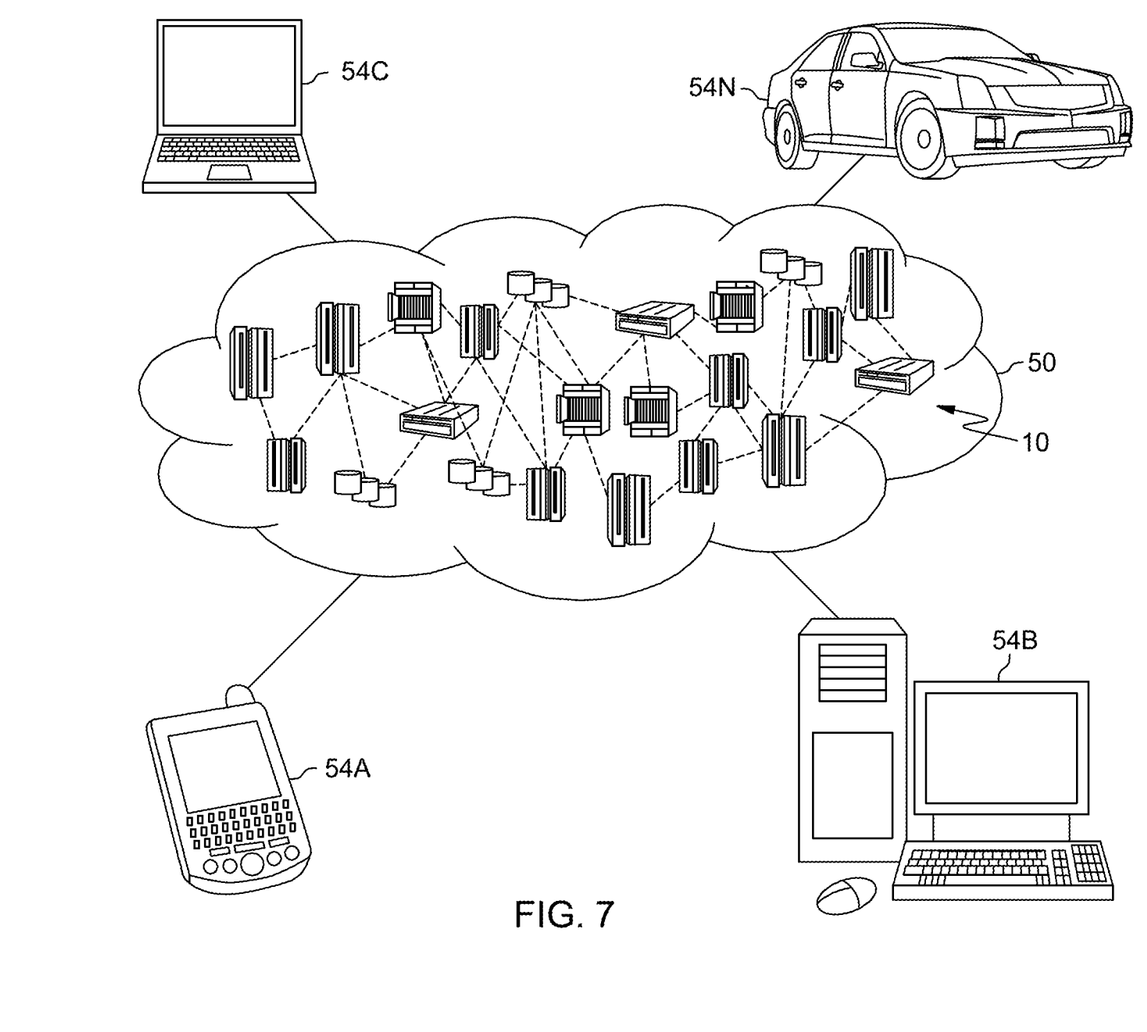
FIG. 7 is a block diagram of one example of a cloud computing environment, in accordance with one or more aspects of the present disclosure.
Figure 8:
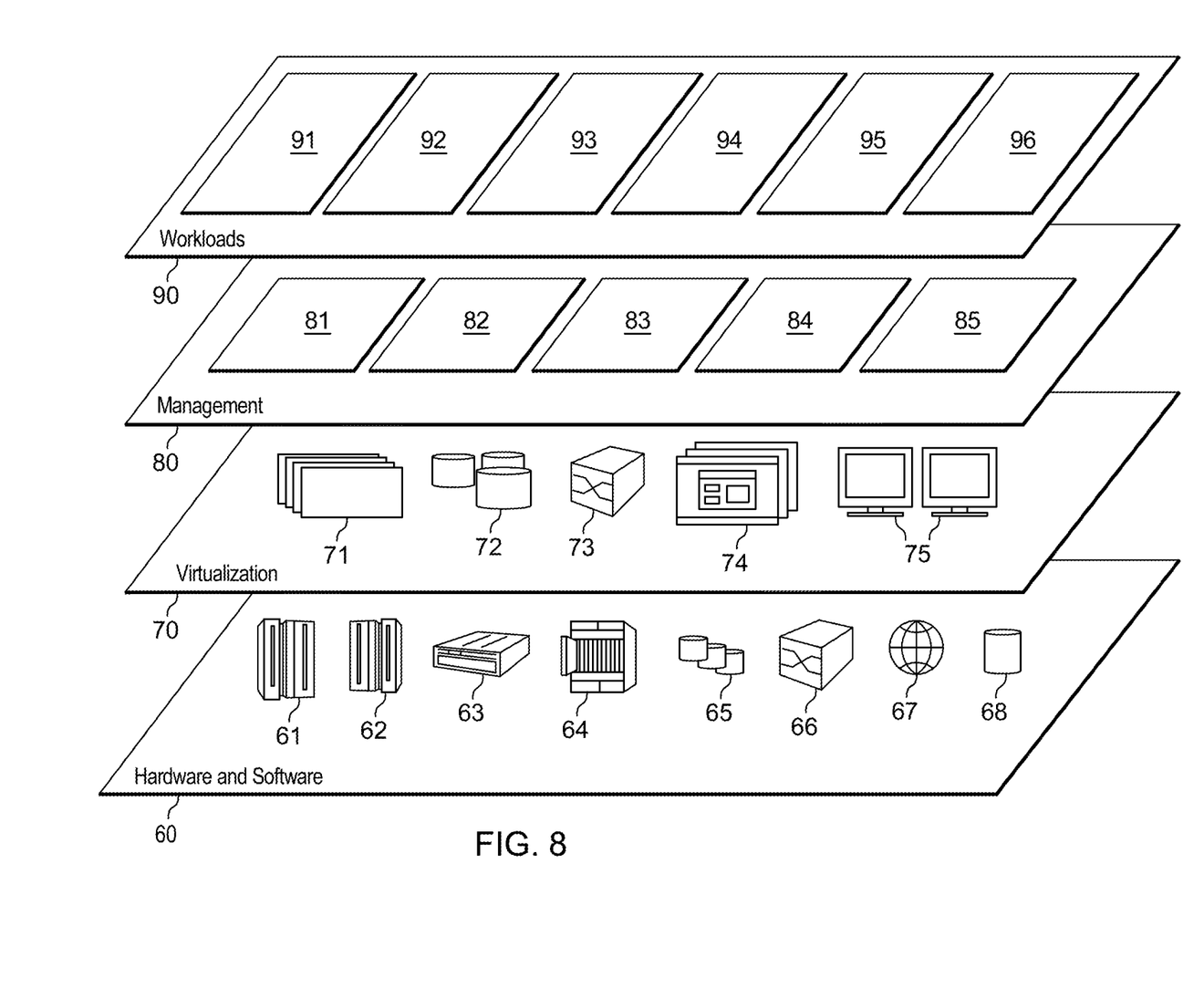
FIG. 8 is a block diagram of one example of functional abstraction layers of the cloud computing environment of FIG. 7, in accordance with one or more aspects of the present disclosure.

FIGS. 6-8 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 6, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 6, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 7 and 8.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. One or more program 40 including program processes 42 can define machine logic to carry out the functions set forth herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch screen display and can be configured to provide user interface functionality, e.g. can facilitate virtual keyboard functionality and input of total data. Computer system 12 in one embodiment can also include one or more sensor device 27 connected to bus 18. One or more sensor device 27 can alternatively be connected through I/O interface(s) 22. One or more sensor device 27 can include a Global Positioning Sensor (GPS) device in one embodiment and can be configured to provide a location of computing node 10. In one embodiment, one or more sensor device 27 can alternatively or in addition include, e.g., one or more of a camera, a gyroscope, a temperature sensor, a humidity sensor, a pulse sensor, a blood pressure (bp) sensor or an audio input device. Computer system 12 can include one or more network adapter 20. In FIG. 4 computing node 10 is described as being implemented in a cloud computing environment and accordingly is referred to as a cloud computing node in the context of FIG. 6.

Referring now to FIG. 7, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for establishing and updating geofence locations as set forth herein. The processing components 96 can be implemented with use of one or more program 40 described in FIG. 7.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

The invention claimed is:

1. A computer-implemented method, comprising:
   analyzing vision-related data regarding a user to determine a currently needed contact lens prescription, resulting in a determined contact lens prescription, wherein the vision-related data comprises a direction, a focal point of an eye gaze of the user, and a focal distance of an object in the eye gaze of the user; and
   adjusting a contact lens prescription of a contact lens atop of the user's eye based on the determined contact lens prescription, wherein the adjusting comprises using an electro-mechanical mechanism to move one or more of a plurality of spherical shaped disks to a desired position relative to a contact lens body, wherein each disk of the plurality of spherical shaped disks corresponds to a unique prescription of the user, the adjusting being based on the vision-related data.

2. The computer-implemented method of claim 1, wherein the adjusting is automatic based on a threshold for the focal distance.

3. The computer-implemented method of claim 1, wherein the analyzing comprises measuring an eye lens of the user.

4. The computer-implemented method of claim 1, wherein the adjusting is one of automatic and controllable by the user.

5. The computer-implemented method of claim 1, wherein the analyzing comprises using one or more camera disposed on the contact lens.

6. The computer-implemented method of claim 1, wherein the vision-related data further comprises vision-related contextual information regarding a current activity of the user, and wherein the analyzing comprises cognitively analyzing the vision-related contextual information.

7. The computer-implemented method of claim 6, wherein the adjusting is one of automatic and controllable by the user.

8. The computer-implemented method of claim 6, wherein the analyzing comprises using one or more camera disposed on the contact lens.

9. The computer-implemented method of claim 6, wherein moving the one or more of the plurality of spherical shaped disks is one of triggering a sliding mechanism to move one or more of the spherical shaped disk based on the determined direction, focal point and focal distance of an object in the user's gaze, and rotating the plurality of spherical shaped disks such that the one or more of the plurality of the spherical shaped disks is at a center portion of the relative to the contact lens body.

10. The computer-implemented method of claim 1, wherein moving the one of the plurality of spherical shaped disks, resulting in a movable disk, comprises sliding the movable disk into the desired position.

11. A contact lens, comprising:
    a spherical shell of a contact lens, the spherical shell having at least one slot therein;
    a first magnification disk of the contact lens, the first magnification disk corresponding to a first prescription, the first magnification disk sized to fit within one or more of the at least one slot; and
    a mechanism of the contact lens, the mechanism moving the first magnification disk into and out of the one or more of the at least one slot.

12. The contact lens of claim 11, wherein the at least one slot comprises at least two slots, the contact lens further comprising a second magnification disk corresponding to a second prescription different than the first prescription, the second magnification disk sized fit within a second slot of the at least two slots, and wherein the mechanism also moves the second magnification disk into and out of the second slot.

13. The contact lens of claim 11, wherein the spherical shell has a second magnification corresponding to a second prescription different from the first prescription.

14. The contact lens of claim 11, wherein the spherical shell has a second magnification and wherein a combination of the second magnification and the first magnification corresponds to a second prescription different from the first prescription.

15. A contact lens, comprising:
    one or more processor;
    a contact lens body;
    a plurality of spherical shaped disks, each of the plurality of spherical shaped disks corresponding to a unique prescription of a user, each spherical shaped disk being smaller than the contact lens body; and a mechanism for moving, by the one or more processor, one of the plurality of spherical shaped disks into a desired position relative to the contact lens body, wherein the one or more processor determines which of the plurality of spherical shaped disks to move, based on current vision-related data regarding the user.

16. The contact lens of claim 15, wherein the mechanism comprises a rotating mechanism.

17. The contact lens of claim 15, wherein the vision-related data is one of: a determined direction, a focal point of a user's gaze and a focal distance of an object in the user's gaze; and vision-related contextual information regarding a current activity of the user.

18. The contact lens of claim 17, further comprising one or more camera disposed on the contact lens for providing the vision-related data.

19. The contact lens of claim 15, wherein the mechanism comprises a sliding mechanism.

20. The contact lens of claim 15, wherein moving the one of the plurality of spherical shaped disks, resulting in a movable disk, comprises rotating the plurality of spherical shaped disks such that the movable disk is in the desired position.

* * * * *